US00PP21603P3

(12) United States Plant Patent
Philley et al.

(10) Patent No.: US PP21,603 P3
(45) Date of Patent: Dec. 28, 2010

(54) ST. AUGUSTINEGRASS PLANT NAMED 'MSA-31'

(50) Latin Name: *Stenotaphrum secundatum*
Varietal Denomination: MSA-31

(75) Inventors: H. Wayne Philley, Mathiston, MS (US); Jeffrey V. Krans, Manitowish, WI (US); Clarence E. Watson, Stillwater, OK (US)

(73) Assignee: Mississippi State University, Mississippi State, MI (US)

( * ) Notice: Subject to any disclaimer, the term of this patent is extended or adjusted under 35 U.S.C. 154(b) by 176 days.

(21) Appl. No.: 12/154,431

(22) Filed: May 22, 2008

(65) Prior Publication Data

US 2009/0293164 P1 Nov. 26, 2009

(51) Int. Cl.
*A01H 5/00* (2006.01)

(52) U.S. Cl. ..... Plt./392

(58) Field of Classification Search ..... Plt./392
See application file for complete search history.

*Primary Examiner*—Kent L Bell
(74) *Attorney, Agent, or Firm*—Lawrence Arthur Schemmel

(57) ABSTRACT

St. Augustinegrass plant 'MSA-31' is a new and distinct variety of perennial St. Augustinegrass cultivar, characterized by its short and narrow leaf blades, fine leaf texture, short internode length and diameter, and superior turf quality and particularly turf density when grown under shade or dense shade. 'MSA-31' is also distinguished by its genetic color and fall and winter color characteristics.

9 Drawing Sheets

Latin name: *Stenotaphrum secundatum.*
Varietal denomination: 'MSA-31'.

BACKGROUND OF THE INVENTION

This invention relates to a new and distinct perennial variety of St. Augustinegrass that is well-suited for turfgrass applications. It is a high-quality, high-density cultivar well-adapted for warm weather climates similar to that found in southern climates where high quality St. Augustinegrass grass cultivar varieties have previously not been available. The Latin name of the genus and species of the new cultivar disclosed herein is *Stenotaphrum secundatum.* This novel hybrid genotype has been given the varietal denomination 'MSA-31' and is a perennial, asexually propagated genotype of St. Augustinegrass, which typically grows vigorously well in warm weather climates and spreads through creeping stolons that root at the nodes contacting soil with adequate moisture. Commonly-known varieties of this genus and species include Raleigh St. Augustine (not patented), 'Floratam' (not patented), B12 (U.S. Plant Pat. No. 16,174 and marketed under the tradename 'Sapphire'™), and SS-100 (U.S. Plant Pat. No. 9,395 and marketed under the tradename 'Palmetto'™). This high quality novel and distinct variety of St. Augustinegrass was first vegetatively propagated at Starkville, Miss. using stolon cuttings and asexually propagated from the time forward to maintain a single genotype.

SUMMARY OF THE INVENTION

The cultivar 'MSA-31' is a new and distinctive variety of St. Augustinegrass characterized by its unique pedigree and very good shade tolerance and high turf quality. The traits of the invention are continually maintained when propagated asexually. This new variety provides an excellent appealing uniform, dense, dark green turf at locations where other St. Augustinegrasses are weakened by excessive shade and disease injury. 'MSA-31' exhibits other excellent qualities and characteristics such as turf density, fine leaf texture, fall and winter color, fast spring green up at warm sites, and excellent low seedhead ratings compared to other St. Augustinegrass cultivars which allow it to be further distinguished from other cultivars.

BRIEF DESCRIPTION OF THE DRAWINGS

FIG. 1 is a flow chart diagram and graphical illustration of the unique pedigree of 'MSA-31' showing the crossing of St. Augustinegrass genotypes resulting in the distinctive new cultivar.

Augustinegrass in the left center, 'Mercedes' in the left background, 'Delmar' in the right foreground, 'Floratam' in the right center, and 'MSA 2-3-98' in the right background.

Figure 6:
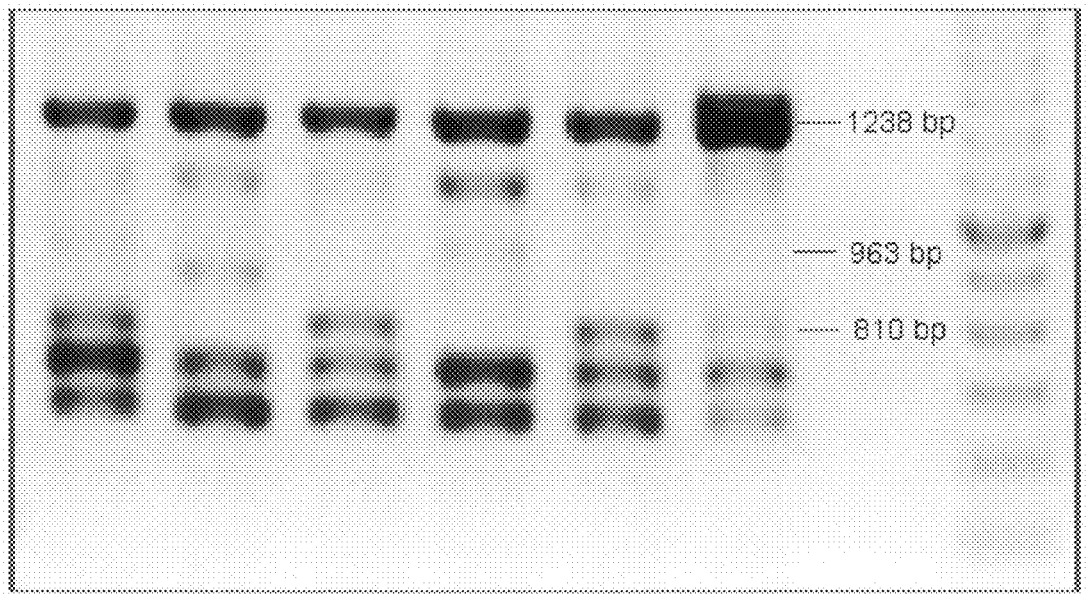

FIG. 6 is a photograph of the unique DNA amplification profile of 'MSA-31' and the DNA profiles of five (5) other St. Augustinegrass cultivars using RAPD primer OPAC20, illustrating that 'MSA-31' is unique and different from 'Sapphire'™, 'Raleigh', 'MSA 2-3-98', 'Palmetto'™, and 'Floratam'.

Figure 7:
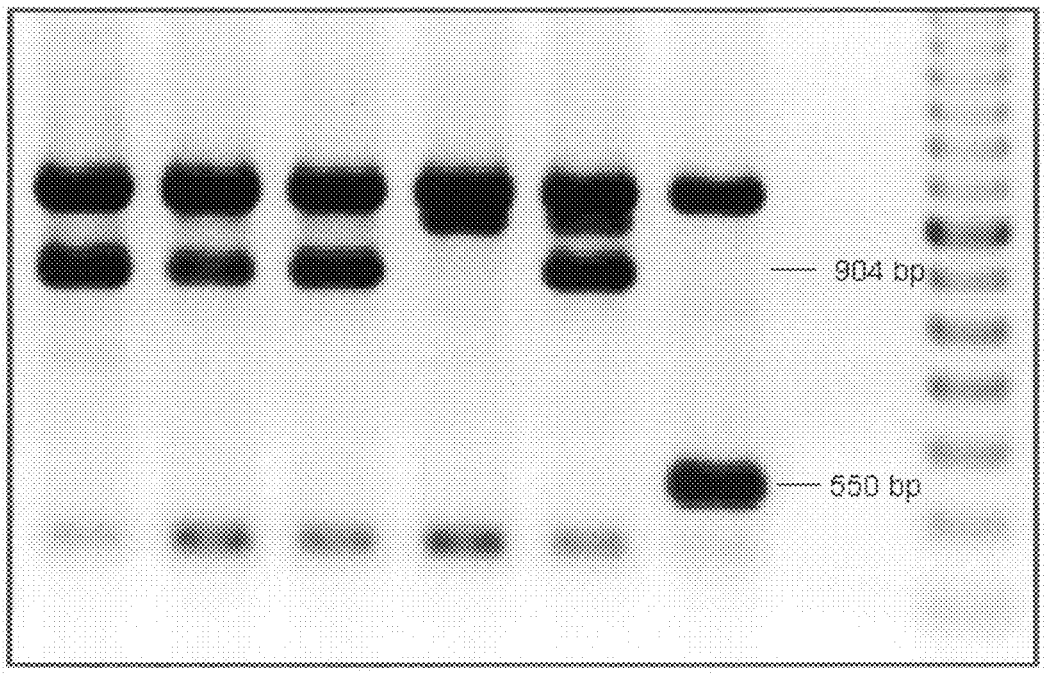

FIG. 7 is a photograph of the unique DNA amplification profile of 'MSA-31' and the DNA profiles of five (5) other St. Augustinegrass cultivars using RAPD primer OPAU1, illustrating that 'MSA-31' is unique and different from 'Sapphire'™, 'Raleigh', 'MSA 2-3-98', 'Palmetto'™, and 'Floratam'.

Figure 8:
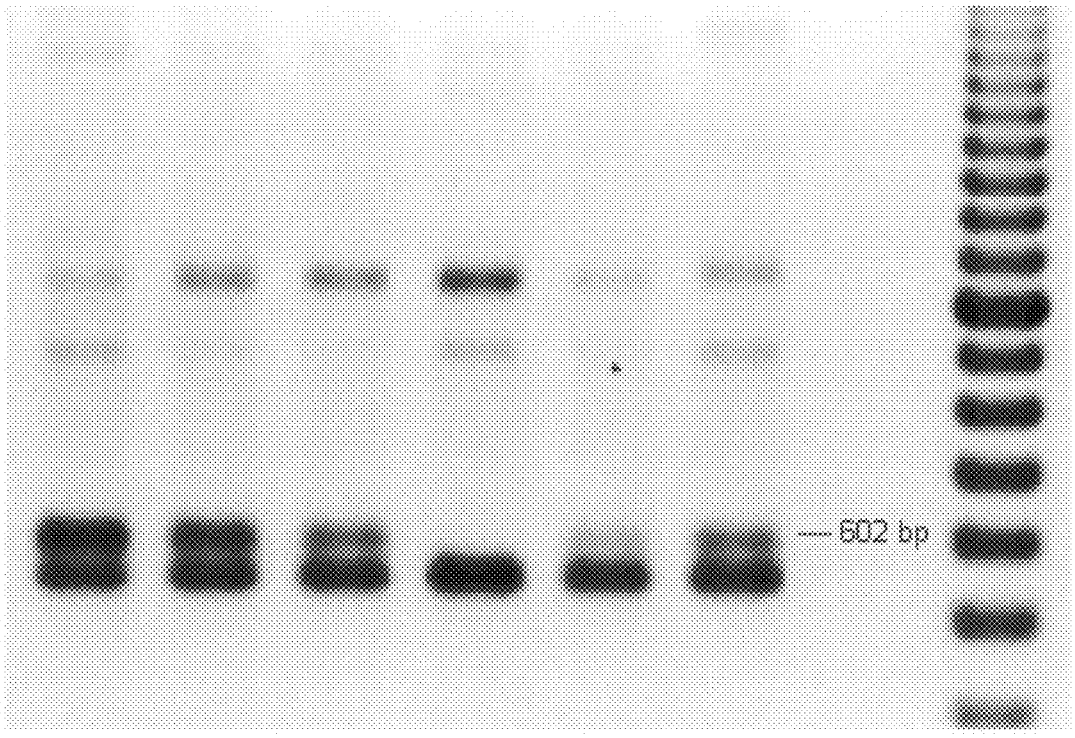

FIG. 8 is a photograph of the unique DNA amplification profile of 'MSA-31' and the DNA profiles of five (5) other St. Augustinegrass cultivars using RAPD primer OPBA9, illustrating that 'MSA-31' is unique and different from 'Sapphire'™, 'Raleigh', 'MSA 2-3-98', 'Palmetto'™, and 'Floratam'.

Figure 9:
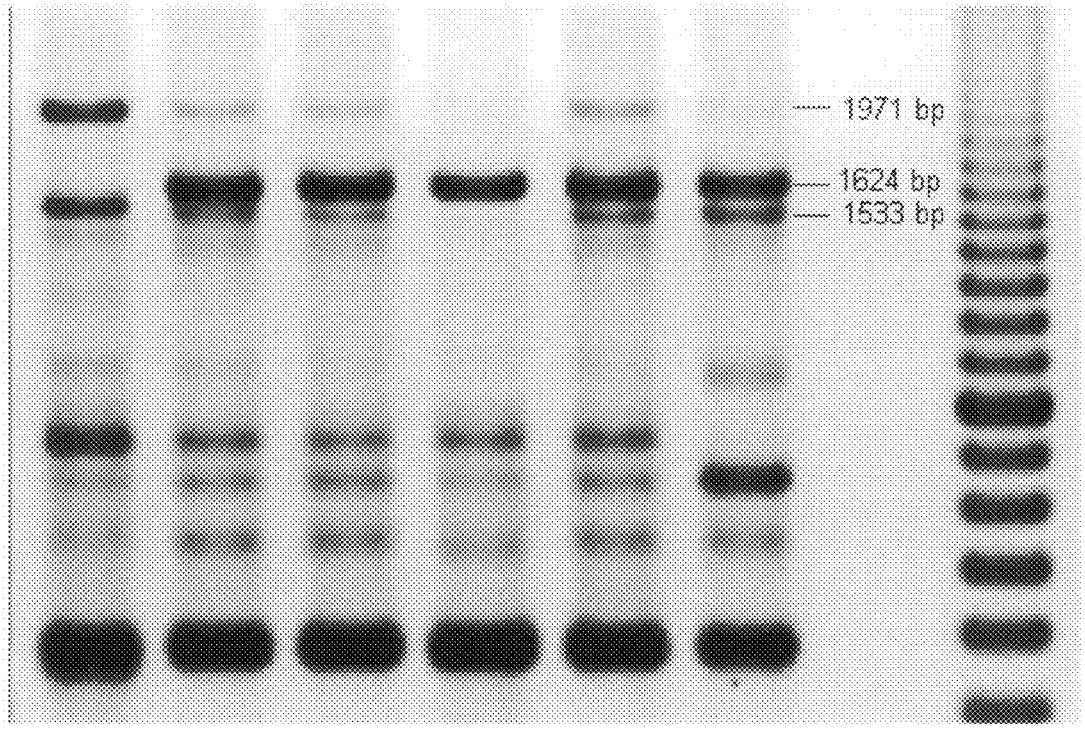

FIG. 9 is a photograph of the unique DNA amplification profile of 'MSA-31' and the DNA profiles of five (5) other St. Augustinegrass cultivars using RAPD primer OPM5, illustrating that 'MSA-31' is unique and different from 'Sapphire'™, 'Raleigh', 'MSA 2-3-98', 'Palmetto'™, and 'Floratam'.

DETAILED BOTANICAL DESCRIPTION OF THE VARIETY

The following is a detailed botanical description of the characteristics of the new *Stenotaphrum secundatum* grass variety known as 'MSA-31', based upon observations of the plant grown under conventional greenhouse conditions and in nursery pots and field plots in Oktibbeha County, Miss. Color notations of plant tissues are based upon the Munsell® Color Chart for plant tissues [*Munsell Book of Color: Glossy Finish Edition,* Munsell Color, Baltimore, Md., 1976; and *Munsell Color Charts for Plant Tissues,* Munsell Color, Baltimore, Md., 1977]. Color notations are affected by light quality and fertility and general plant growth. Certain characteristics will vary depending on the age of the plants, such that characteristics such as dimensions, sizes, and colors are approximations or averages since the variety has not been observed under every possible environmental condition. Therefore, the phenotype of the variety may differ from the descriptions depending upon environmental variations including, but not limited to, the season, temperatures, day lengths, light direction and quality, and fertilization, as well as other factors.

'MSA-31' is a high quality, high density, perennial, vegetatively (asexually) propagated genotype of St. Augustinegrass. It is well-adapted for turf applications in southern and warmer locations typically where 'Floratam', the most popular St. Augustinegrass cultivar, is used. 'MSA-31' is capable of sustaining high turf quality and excellent density ratings in shade. The creeping or ascendant stolons of 'MSA-31' are dorsiventrally compressed and root adventitiously at the nodes. The leaf blade color of both the upper surface and lower surface of the leaf blade color is dark green and is rated 7.5 GY 4/4 for field-grown plots and 7.5 GY 4/4 to 4/6 for greenhouse-grown pots, both ratings based on the Munsell® Color Chart for plant tissue. The color chart match was completed using natural sunlight with no supplemental lighting for the 'MSA-31' cultivars in the field-grown plots and the greenhouse-grown pots, both in the month of May. 'MSA-31' has a green internode color rated 7.5 GY 4/4 based on the Munsell® Color Chart that is fairly stable, in contrast to the internodes of other St. Augustinegrass cultivars that may change to various shades of purple with cooler temperatures, such as 'Floratam' in particular. 'MSA-31' typically has yellow anthers and white stigmas and has an unreduced chromosome number of 18.

The leaf texture of 'MSA-31' is finer than 'Raleigh' and 'Floratam' St. Augustinegrasses. 'MSA-31' has better cold resistance or tolerance than 'Floratam' but less than 'Raleigh', typically considered the cold tolerance standard. 'MSA-31' is recommended for U.S. Department of Agriculture (USDA) plant hardiness zones 8 and higher, but not necessarily recommended for sites or locations where winterkill of St. Augustinegrasses is a problem.

Unique Pedigree and Origin of 'MSA-31'

'MSA-31' St. Augustinegrass cultivar resulted from a cross of two diploid St. Augustinegrass plants selected for their specific superior qualities. 'MSA-31' resulted from an F1 plant (F1 refers to first generation) cross between 'Seville' St. Augustinegrass (U.S. Plant Pat. No. 4,097, issued Sep. 6, 1977, now expired) and 'MSA-10', an experimental cultivar selected for cold tolerance, at Starkville, Miss. Six (6) plants were produced from this cross. 'MSA-31' was selected over all its siblings for its high turf density and quality. The original, single seed that produced 'MSA-31' was germinated in a temperature-controlled germination chamber. The seedling was transplanted to a pot grown in a greenhouse and eventually transplanted to a field nursery. From that point in time forward, 'MSA-31' has been vegetatively propagated and has consistently and completely been stably reproduced by the aforementioned asexual propagation. FIG. 1 shows the pedigree of 'MSA-31' in a flowchart format. In FIG. 1, 'Seville' is a highly fertile, semi-dwarf diploid cultivar selected for its high density and fine leaf texture but not necessarily for its cold tolerance. 'MSA-10' is a Mississippi St. Augustinegrass experimental cultivar from Starkville, Miss. selected for cold tolerance and winter survival. The unique origin of 'MSA-31' shown distinguishes it from other commercially produced St. Augustinegrass varieties in that most of such varieties are of unknown origin. The pedigree of 'MSA-31' is unique in that its parents are known. As a result, 'MSA-31' has higher turf quality and higher turf density, particularly in shade and in dense tree shade, than either of its ancestors.

Morphology of 'MSA-31'

The morphological characteristics of 'MSA-31' also distinguish it from other St. Augustinegrass cultivars. To measure morphological characteristics, five (5) four-inch plugs of each of four (4) St. Augustinegrass cultivars were harvested from established field plots at Starkville, Miss. in March, 2006. These twenty (20) plugs were washed free of soil and transplanted to six-inch pots filled with commercial potting mix. These twenty (20) plugs were grown non-mown in a greenhouse for six (6) weeks before measurements were initiated. All stolons that grew out from the original plug were systematically evaluated, beginning with the youngest visible internode and proceeding backward toward the pot. Measurements included diameter and length of all internodes and width and length of all leaf blades.

Figure 2:
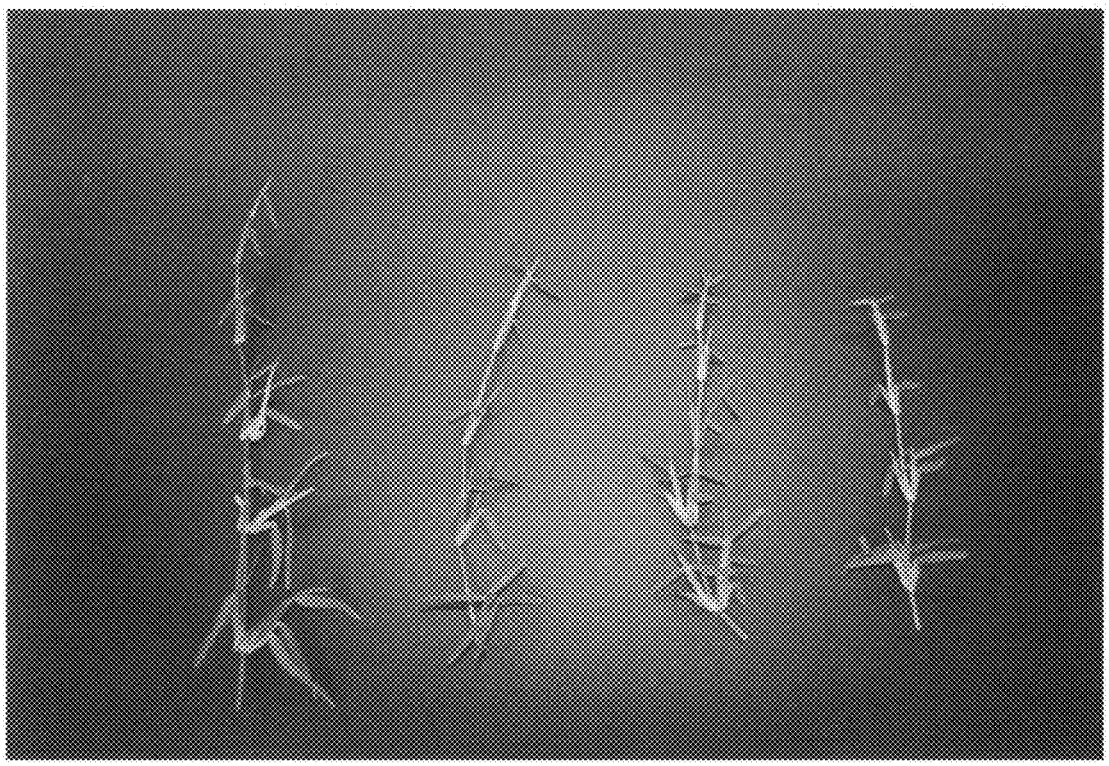
FIG. 2 is a color photograph taken on Apr. 24, 2006 at greenhouses in Starkville, Miss. of stolon segments of four (4) St. Augustinegrass cultivars that compares and illustrates the distinct morphologies of each segment. From left to right, 'Floratam' with its long leaves and purple internodes is shown on the far left. Next in line to the right is 'Raleigh' with its long leaves and green/yellow internodes. Next in line to the right is 'MSA 2-3-98' with its small leaves and green internodes. Finally on the far right, 'MSA-31' is shown with its small leaves and dark green internodes.
Figure 3:
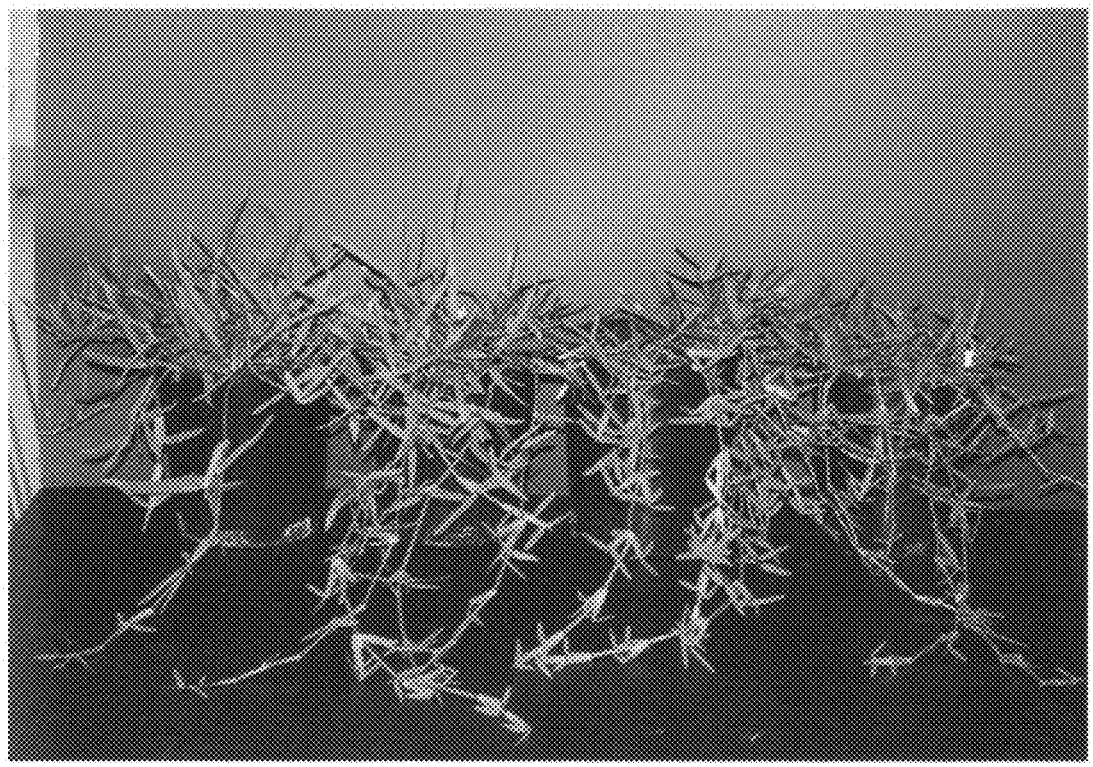
FIG. 3 is a color photograph taken on Apr. 24, 2006 at greenhouses in Starkville, Miss. of four (4) whole non-mown St. Augustinegrass cultivar plants in growing pots showing, from left to right: 'Floratam' with its longer leaves, tall stature, and purple/red internodes; 'Raleigh' with its longer leaves, tall stature, and green/yellow internodes; 'MSA 2-3-98' with its smaller leaves, shorter stature, and more green internodes; and 'MSA-31' with its small leaves, shorter stature, and darker green internodes.
Figure 4:
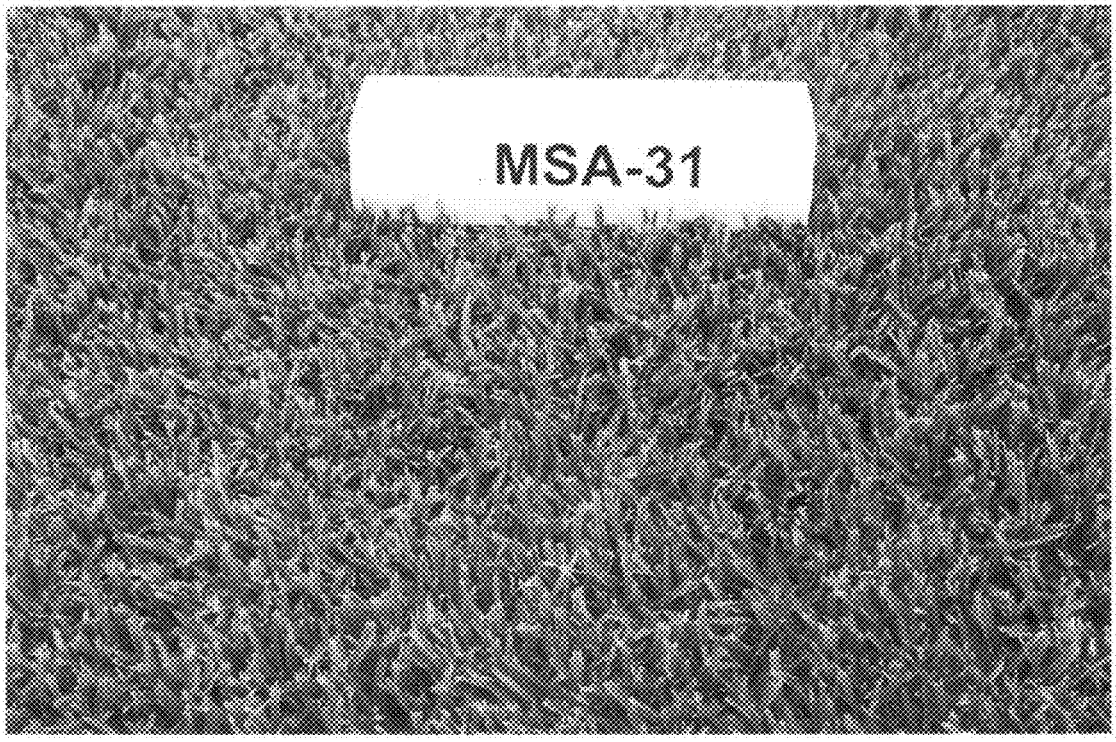
FIG. 4 is a color photograph taken on Oct. 26, 2004 at Starkville, Miss. during the 2002 NTEP test showing the turf density of the 'MSA-31' St. Augustinegrass cultivar.

The non-mown leaf blade length of 'MSA-31' was significantly shorter than that of cultivars 'Floratam' and 'Raleigh' but similar to Mississippi experimental cultivar 'MSA 2-3-98' (Table 1 and FIG. 2). FIG. 2 shows stolons of four (4) St. Augustinegrass cultivars that illustrate different or comparative morphologies, from left to right: 'Floratam', 'Raleigh', 'MSA 2-3-98' and 'MSA-31'. FIG. 3 shows the same four cultivars as whole non-mown plants in growing pots and shows the smaller morphology of 'MSA-31'. FIG. 4 shows a close-up photograph of the 2002 NTEP test plot of 'MSA-31' and, specifically, 'MSA-31''s excellent density characteristics. The leaf blade width of 'MSA-31' was significantly narrower than 'Floratam' and 'Raleigh' and not significantly wider than 'MSA 2-3-98'. The internode length of 'MSA-31' was significantly shorter than 'Floratam', 'Raleigh', and 'MSA 2-3-98'. The internode diameter of 'MSA-31' was significantly smaller than 'Floratam', 'Raleigh', and 'MSA 2-3-98'. (Table 1). 'MSA-31' also differs visually from other cultivars in other respects. For example, 'MSA-31''s yellow anthers and white stigmas are similar to certain cultivars, such as the white stigmas of 'Raleigh' and 'Palmetto'™, but different from 'Palmetto'™'s and 'Floratam''s orange-yellow anthers, 'Floratam''s purple stigmas, and 'Sapphire'™'s gray-orange anthers and purple-violet stigmas.

The non-mown plant height of 'MSA-31' is approximately 15 centimeters (cm). The internode diameter is approximately 2.48 millimeters (mm) (Table 1) and the internode and leaf blade color are rated 7.5 GY 4/4 based on the Munsell® Color Chart. The leaf apex is obtuse and the margin is entire.

The inflorencence of 'MSA-31' is a spike-like raceme. The floral region of a mature inflorescence has a mean length of 43 mm. The mean length of the peduncle is 41 mm. Spikelets are embedded in one side of a thickened rachis. The mean width of a dried rachis of 'MSA-31' is 3.0 mm. Spikelets are most often solitary, but may be paired, and are positioned in two rows. When paired, one spikelet is borne on a 2-3 mm pedicel, the other is sessile. The mean number of spikelets per raceme is 12. Each spikelet is ovoid and 4.0-4.5 mm in length. On each spikelet the outer glume is 1 mm in length, followed by two florets—one staminate and one fertile. The sterile lemma and palea and fertile lemma and palea are nearly equal in length (4.0-4.5 mm). Seed, if produced, are oblong and brown in color with a mean length of 1.8 mm.

The new 'MSA-31' cultivar has a fibrous root system with a typical root length of approximately 17 cm, a typical root diameter of approximately 6 mm, and a typical root color of white. 'MSA-31' has no rhizomes.

TABLE 1

Morphology measurements of St. Augustinegrass cultivars grown in non-mown pots.

| Cultivar | Leaf Blade Length mm | Leaf Blade Width mm | Internode Length mm | Internode Diameter mm |
|---|---|---|---|---|
| 'Floratam' | 63.9 | 8.9 | 62.2 | 3.54 |
| 'Raleigh' | 34.3 | 7.6 | 67.1 | 3.11 |
| 'MSA 2-3-98' | 27.9 | 6.6 | 53.0 | 2.98 |
| MSA-31' | 27.9 | 6.5 | 49.0 | 2.48 |
| LSD (0.05) | 4.1 | 0.3 | 2.9 | 0.06 |

Turf Performance Evaluations

Turfgrass performance evaluation ratings in multiple tests likewise distinguish 'MSA-31' from other St. Augustinegrass varieties.

Florida Test

'MSA-31' was first evaluated at Gainesville, Fla. in the years 1995-1998 along with eleven (11) other St. Augustinegrass cultivars. Grasses were replicated four (4) times in a randomized complete block design. As shown in Tables 2 through 5, the 'MSA' cultivars were Mississippi St. Augustinegrass experimental cultivars from Starkville, Miss. The 'FHSA' cultivars were Florida Hawaii St. Augustinegrass experimental cultivars collected in Hawaii and tested at Florida. The 'FL' cultivar was a Florida experimental cultivar. The establishment of 'MSA-31' was not as good as 'Raleigh', but generally better than 'Palmetto' and 'Floratam', and significantly better than Seville in this test (Table 2). 'MSA-31' received consistently high turf quality ratings (Table 3) and, in 1996, the turf quality rating of 'MSA-31' was significantly higher than any other cultivar in the test. Turf density was rated for two years. 'MSA-31' received higher turf density ratings than 'Floratam', 'Raleigh', 'Palmetto', and 'Seville' in each year and, in fact, rated higher than all twelve cultivars tested in both years (Table 4). In 1998, this test rated leaf texture and seedhead production (Table 5). The leaf texture of 'MSA-31' was finer than all but two other cultivars and significantly finer than 'Raleigh' and 'Floratam'. Seedhead production of 'MSA-31' was less than all but one other cultivar and significantly less than the two 'MSA' cultivars and 'Raleigh' and 'Palmetto'.

TABLE 2

Average percent ground cover estimates of St. Augustinegrass selections during establishment at Gainesville, FL.

| | 1995 | | | 1996 | |
|---|---|---|---|---|---|
| Cultivar | September | October | November | April | May |
| 'Raleigh' | 26 | 31 | 33 | 41 | 52 |
| 'FL-1997-6' | 28 | 29 | 31 | 42 | 51 |
| 'MSA-11' | 24 | 27 | 29 | 41 | 46 |
| 'MSA-31' | 22 | 23 | 25 | 32 | 42 |
| 'Palmetto' | 19 | 20 | 21 | 34 | 41 |
| 'MSA-10' | 15 | 18 | 23 | 35 | 42 |
| 'Floratam' | 12 | 17 | 21 | 34 | 42 |
| 'Floralawn' | 12 | 16 | 21 | 31 | 40 |
| 'Floratine' | 9 | 14 | 18 | 30 | 36 |
| 'FHSA-115' | 9 | 12 | 15 | 27 | 34 |
| 'FSHA-117' | 8 | 10 | 13 | 24 | 31 |
| 'Seville' | 5 | 5 | 5 | 12 | 16 |
| MSD(0.05) | 3 | 3 | 4 | 5 | 6 |

| | 1996 | | | |
|---|---|---|---|---|
| Cultivar | June | July | August | September |
| 'Raleigh' | 81 | 92 | 93 | 97 |
| 'FL-1997-6' | 74 | 90 | 93 | 95 |
| 'MSA-11' | 73 | 85 | 88 | 96 |
| 'MSA-31' | 73 | 84 | 89 | 95 |
| 'Palmetto' | 69 | 83 | 87 | 93 |
| 'MSA-10' | 69 | 82 | 87 | 91 |
| 'Floratam' | 64 | 80 | 86 | 92 |
| 'Floralawn' | 68 | 81 | 86 | 92 |
| 'Floratine' | 60 | 72 | 82 | 91 |
| 'FHSA-115' | 57 | 73 | 81 | 88 |
| 'FSHA-117' | 55 | 71 | 81 | 91 |
| 'Seville' | 34 | 50 | 61 | 66 |
| MSD(0.05) | 10 | 8 | 5 | 5 |

TABLE 3

Turf quality ratings of St. Augustinegrass selections at Gainesville, FL. (1 = poor, 9 = excellent)

| Cultivar | 1996 | 1997 | 1998 |
|---|---|---|---|
| 'MSA-31' | 7.6 | 5.6 | 5.4 |
| 'FSHA-117' | 6.3 | 5.5 | 5.6 |
| 'MSA-11' | 6.3 | 5.4 | 5.6 |
| 'Floratine' | 6.2 | 6.0 | 5.9 |
| 'Floratam' | 6.2 | 5.7 | 5.3 |
| 'FHSA-115' | 6.1 | 5.5 | 5.4 |
| 'FL-1997-6' | 5.9 | 6.0 | 6.9 |
| 'Floralawn' | 5.9 | 5.5 | 5.1 |
| 'Raleigh' | 5.4 | 4.6 | 4.6 |
| 'Palmetto' | 5.2 | 5.2 | 5.5 |
| 'MSA-10' | 5.1 | 4.7 | 4.8 |
| 'Seville' | 3.8 | 4.3 | 5.3 |
| MSD (0.05) | 1.0 | 1.0 | 0.9 |

TABLE 4

Turf density ratings of St. Augustinegrass selections at Gainesville, FL. (1 = low, 9 = high)

| Cultivar | 1996 | 1997 |
|---|---|---|
| 'MSA-31' | 8.6 | 7.3 |
| 'FL-1997-6' | 7.3 | 7.2 |
| 'MSA-11' | 7.2 | 7.1 |
| 'FSHA-117' | 7.1 | 6.5 |
| 'Floratine' | 6.9 | 6.5 |
| 'FHSA-115' | 6.8 | 6.2 |
| 'Floratam' | 6.5 | 6.1 |
| 'Palmetto' | 6.4 | 6.6 |
| 'Raleigh' | 6.4 | 6.1 |
| 'Floralawn' | 6.4 | 5.8 |
| 'MSA-10' | 6.2 | 6.2 |
| 'Seville' | 5.3 | 5.7 |
| MSD (0.05) | 0.8 | 0.7 |

TABLE 5

Leaf texture and seedhead production of St. Augustinegrass selections at Gainesville, FL in 1998. (Texture: 1 = coarse, 9 = fine)

| Cultivar | Leaf texture | Seedheads[+] |
|---|---|---|
| 'MSA-10' | 6.8 a* | 5.0 a |
| 'MSA-31' | 6.0 ab | 1.1 fg |
| 'FL-1997-6' | 6.0 ab | 1.9 de |
| 'MSA-11' | 5.8 bc | 4.1 bc |
| 'Seville' | 5.5 bc | 1.0 g |
| 'Palmetto' | 5.2 bcd | 3.5 c |
| 'Raleigh' | 5.0 cd | 4.4 ab |
| 'FHSA-115' | 5.0 cd | 1.5 efg |
| 'Floratine' | 4.5 de | 2.4 d |
| 'FSHA-117' | 3.8 ef | 1.8 def |
| 'Floratam' | 3.0 f | 1.6 efg |
| 'Floralawn' | 3.0 f | 1.5 efg |

[+]Seedheads visually rated on a 1 to 5 scale where 1 = no seedheads and 5 = most seedheads. Values are average of 8 observations.

*Means within columns with same letter are not significantly different (P = 0.05) using the Waller-Duncan k-ratio t-test.

Lawrenceburg, Tennessee Test

A St. Augustinegrass cultivar trial was conducted at Lawrenceburg, Tenn. in the years 2002-2005. Eight (8) St. Augustinegrass cultivars, including 'Raleigh', 'Floratam', 'MSA-31', and other experimental cultivars, were planted in a randomized complete block design with three (3) replications. 'MSA-31' received high turf quality ratings in the Lawrenceburg test (Table 6). The cold tolerance of 'MSA-31' shows lower percent green plot cover ratings in the spring, although its percent green plot cover rating in the fall of 2003 was exceptionally high (Table 7). Due to the severe winter of 2004-05, all test cultivars suffered winter injury as shown in the May 12, 2005 measurements of Table 7. 'MSA-31' displayed good color and good turf density and color with moderate symptoms of gray leaf spot (Table 8). 'MSA-31' demonstrated the best color rating of all cultivars tested and a better turf density rating than all but two of the cultivars in the test.

TABLE 6

Turf quality of St. Augustinegrass test at Lawrenceburg, TN. (1 = poor, 9 = excellent)

| Cultivar | 2002 | 2003 | 2004 | 2005 | 2002-2005 |
|---|---|---|---|---|---|
| 'MSA 2-3-98' | 7.0 | 8.0 | 7.7 | 7.3 | 7.5 |
| 'MSA-10-4-98' | 6.7 | 7.3 | 7.6 | 6.0 | 6.9 |
| 'MSA-31' | 7.0 | 8.0 | 6.4 | 5.3 | 6.7 |
| 'Raleigh' | 6.0 | 7.3 | 6.5 | 5.7 | 6.4 |
| 'MSA-8-6-98' | 5.3 | 5.7 | 6.0 | 6.7 | 5.9 |
| 'MSA-5-5-98' | 5.3 | 4.7 | 5.3 | 5.3 | 5.2 |
| 'Floratam' | 4.7 | 4.3 | 4.2 | 2.3 | 3.9 |
| 'MSA-13-6-98' | 4.3 | 2.3 | 3.5 | 4.3 | 3.6 |
| LSD (0.05) | 1.2 | 2.2 | 2.2 | 2.2 | 1.6 |

TABLE 7

Percent green plot cover of St. Augustinegrass test at Lawrenceburg, TN.

| Cultivar | May 18, 2003 | Nov. 13, 2003 | May 5, 2004 | May 12, 2005 | Aug. 18, 2005 |
|---|---|---|---|---|---|
| 'MSA 2-3-98' | 95.0 | 100.0 | 70.0 | 25.0 | 91.7 |
| 'Raleigh' | 86.7 | 100.0 | 60.0 | 25.0 | 81.7 |
| 'MSA-10-4-98' | 71.7 | 95.0 | 50.0 | 6.7 | 81.7 |
| 'MSA-8-6-98' | 70.0 | 66.7 | 56.7 | 38.3 | 76.7 |
| 'MSA-13-6-98' | 50.3 | 16.7 | 43.3 | 21.7 | 51.7 |
| 'MSA-5-5-98' | 46.7 | 56.7 | 43.3 | 35.0 | 68.3 |
| 'MSA-31' | 21.7 | 98.3 | 16.7 | 4.7 | 53.3 |
| 'Floratam' | 3.7 | 53.3 | 3.3 | 2.7 | 20.0 |
| LSD (0.05) | 35.7 | 32.2 | 27.1 | 20.3 | 33.9 |

TABLE 8

Color, density, and gray leaf spot ratings of the St. Augustinegrass test at Lawrenceburg, TN rated on Aug. 18, 2005.

| Cultivar | Color | Density | Gray Leaf Spot[a] |
|---|---|---|---|
| 'MSA 2-3-98' | 7.3 | 7.0 | 8.0 |
| 'MSA-31' | 7.7 | 6.0 | 5.0 |
| 'MSA-10-4-98' | 7.0 | 6.0 | 6.7 |
| 'Raleigh' | 6.7 | 5.7 | 7.0 |
| 'MSA-8-6-98' | 6.0 | 5.7 | 6.7 |
| 'Floratam' | 5.3 | 4.0 | 2.0 |
| 'MSA-5-5-98' | 6.0 | 3.7 | 5.7 |
| 'MSA-13-6-98' | 4.3 | 3.0 | 4.3 |
| LSD (0.05) | NS | 2.3 | 2.4 |

Figure 5:
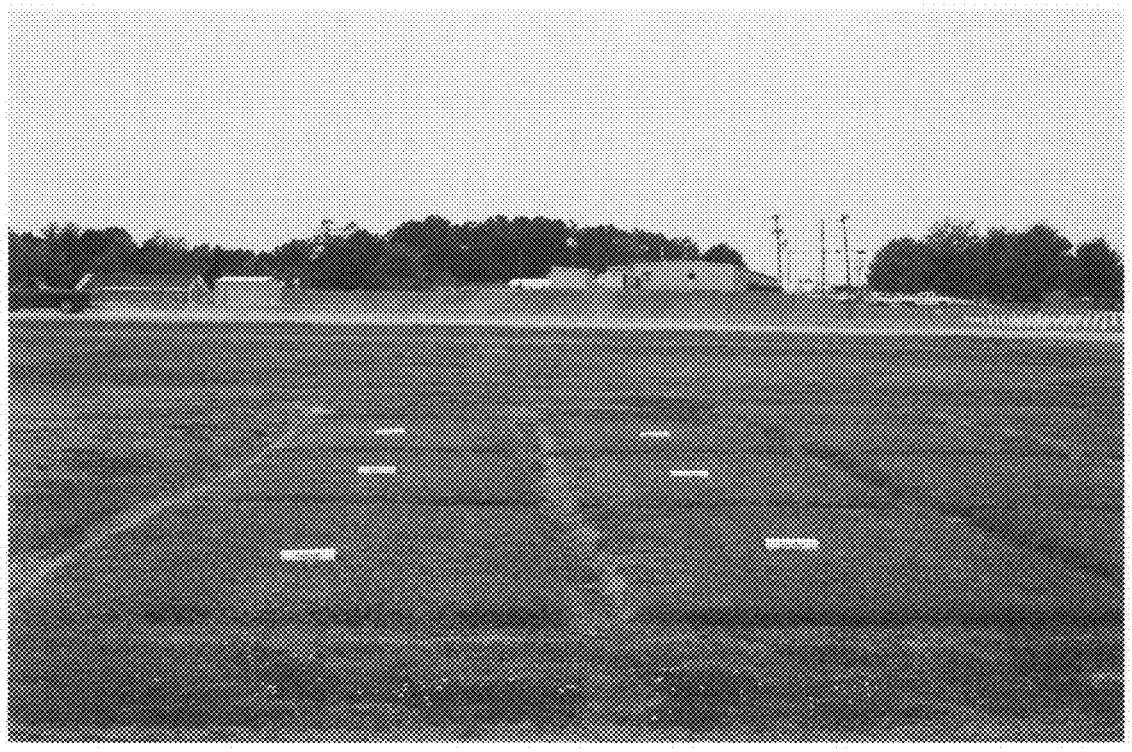
FIG. 5 is a color photograph taken on Oct. 26, 2004 at Starkville, Miss. during the 2002 NTEP test showing field plots of six (6) cultivars (1 full replication), specifically depicting 'Raleigh' in the left foreground, 'MSA-31' St.

[a] Gray leaf spot rating scale: 1 = severe, 9 = no disease
Color scale: 1 = light green, 9 = dark green
Density scale: 1 = low, 9 = high National Turfgrass Evaluation Program Test 'MSA-31' was entered into the 2002 National St. Augustinegrass Test coordinated by the National Turfgrass Evaluation Program (NTEP). This multiple-environment testing provided the best available and the most definitive data on the performance characteristics of 'MSA-31' compared to other commercial and experimental St. Augustinegrass cultivars. The nine (9) test sites included Pomona, Calif.; Jay, Fla.; Griffin, Ga.; Savannah, Ga.; Calhoun, La.; Starkville, Miss.; Lane, Okla.; Florence, S.C.; and College Station, Tex. Each site test included each variety listed in Tables 9 through 29. The specified experimental design at each site was a randomized complete block with three (3) replications of each variety tested. All cultivars were established by planting eighteen (18) 3-inch plugs in each plot. At each site, 'MSA-31' was compared to 'MSA 2-3-98', 'Delmar', 'Floratam', 'Mercedes', and 'Raleigh'. FIG. 5 shows field plots of 'MSA-31' and five other cultivars in the 2002 NTEP test at the Starkville, Miss. site.

Establishment rate was determined by estimating percent plot coverage at monthly intervals and dividing by the number of ratings to arrive at a mean. Table 9 represents the establishment rates of the six (6) cultivars at six (6) of the nine (9) test locations. 'MSA-31' established slower from plugs than 'Floratam' at each location due most likely to 'MSA-31''s significantly shorter internode length.

Tests were established at three (3) locations (Calhoun, La.; Starkville, Miss.; and Lane, Okla.) and data was submitted on turfgrass quality ratings in full sun in 2002 (Table 10). 'MSA-31' received the highest turfgrass quality rating of all cultivars except one at Calhoun and the best turfgrass quality rating at Lane, both in full sun. Its turfgrass quality ratings were significantly higher than 'Floratam' at all three sites and significantly higher than 'Raleigh' at Calhoun and Lane. Other sites were subsequently established and data was reported beginning in 2003 (Table 11). When considered across eight (8) sites where the cultivars were grown in full sun, 'MSA-31' received a 4-year average turfgrass quality rating that was slightly higher than 'Raleigh', 'Floratam', and 'Delmar' and not significantly lower than 'MSA 2-3-98' and 'Mercedes'. As Table 11 shows, 'MSA-31' ranked the highest in turfgrass quality at Pomona.

A dense shade site was planted at Savannah, Ga. in 2002 and turfgrass quality ratings data began to be reported early in 2003 (Table 12). 'MSA-31' consistently ranked at or near the top for turfgrass quality under dense shade at this site, ranking the best for 2003, 2004, and 2006 and better than all but one cultivar for 2005. 'MSA-31' had the highest mean turfgrass quality rating under dense shade for 2003-2006.

The exceptional turfgrass quality of 'MSA-31' under dense shade is significant, particularly since the effects of shade generally cause lower turf density. As shown in Table 13, 'MSA-31' maintained exceptionally high average turfgrass density ratings under dense shade at this site during both the summer and fall seasons.

Five (5) sites provided leaf texture ratings of St. Augustinegrass cultivars from 2003 to 2006 (Table 14). 'MSA-31' was rated consistently fine textured at each site and was rated as having the finest leaf texture at Pomona from 2003 to 2005. When averaged across all five (5) sites over four (4) years, 'MSA-31' ranked finer than all other cultivars tested.

Genetic color ratings should generally be conducted when turfgrass is actively growing and is not under stress in order to reflect the inherent color of the cultivar. Genetic color in this test was rated at seven (7) sites during 2003-2006. When averaged across all sites, the genetic color rating of 'MSA-31' ranked in the middle and was not significantly different from the other cultivars, although it ranked as having one of the three best color ratings at the Pomona site (Table 15). Fall and winter color ratings are used to assess color retention during the fall and winter months, respectively. Table 16 and Table 17 show high fall and winter color retention of 'MSA-31' at sites that did not experience much frost. The frost tolerance of 'MSA-31' was lower at some test locations (Table 18).

Similar to the Lawrenceburg, Tenn. test evaluation data, 'MSA-31' suffered winter injury at colder locations during the NTEP test. Percent winter kill estimates of 'MSA-31' were high at the Lane and Florence sites (Table 19). Spring green-up of St. Augustinegrasses is affected by the amount of low-temperature injury in the winter. 'MSA-31' was slower to green-up in the spring than some cultivars at colder test sites, including Griffin, Starkville, Lane, and Florence, but was the fastest or one of the fastest to green-up at warmer sites such as Pomona, Jay, and College Station (Table 20). Low temperatures also affected estimates of percent living ground cover in spring (Table 21). 'MSA-31' displayed lower coverage in spring at the colder sites.

'MSA-31' was less susceptible than four (4) of the six (6) cultivars to warm temperature brown patch disease (*Rhizoctonia solani*) at the Florence and College Station sites (Table 22) and less susceptible than all other cultivars to cool temperature brown patch disease (*Rhizoctonia cerealis*) at the Florence site (Table 23). Gray leaf spot was not as severe on 'MSA-31' as on other cultivars at test sites in Florida, Mississippi, and Oklahoma (Table 24). 'MSA-31' was more susceptible than 'Raleigh' and 'Floratam' to take-all patch (*Gaumanomyces graminis*) at the Lane site in 2004 (Table 25).

The production of seedheads (inflorescence) in turf is undesirable. Seedhead production of the cultivars in the NTEP test was measured at the Lane site (Table 26) and the Starkville site (Table 27). At both sites, 'MSA-31' produced fewer seedheads than both 'Raleigh' and 'Delmar'.

The horizontal spread rating of the St. Augustinegrass cultivars was rated at the Lane site in 2004 (Table 28). The horizontal spread of 'MSA-31' was rated significantly slower than 'Floratam' and, as with establishment rate, was likely due to the shorter internode length of 'MSA-31'. Once established, however, 'MSA-31' may require less frequent edging around sidewalks and beds.

Chinch bug (*Blissus insularis*) populations can be devastating on St. Augustinegrass turf. 'Floratam' St. Augustinegrass generally has a high resistance to this small insect pest. Chinch bugs were counted at the NTEP St. Augustinegrass test at the Griffin site in 2006 (Table 29). Numbers of chinch bugs for 'MSA-31' were significantly higher than 'Floratam' but significantly lower than 'Raleigh'.

TABLE 9

Establishment rate of cultivars in the 2002 National St. Augustinegrass Test.

| Cultivar | Calhoun, LA | College Station, TX | Starkville, MS |
|---|---|---|---|
| 'Floratam' | 83.3% | 78.3% | 81.6% |
| 'Raleigh' | 63.3 | 60.0 | 81.9 |
| 'MSA 2-3-98' | 71.7 | 36.7 | 73.1 |
| 'Mercedes' | 73.3 | 48.3 | 76.7 |
| 'MSA-31' | 70.0 | 28.3 | 73.3 |
| 'Delmar' | 46.7 | 36.7 | 69.2 |
| LSD | 16.6 | 21.4 | 7.9 |
| **Cultivar** | **Pomona, CA** | **Jay, FL** | **Lane, OK** |
| 'Floratam' | 92.6% | 41.7% | 92.2% |
| 'Raleigh' | 88.1 | 17.2 | 77.6 |
| 'MSA 2-3-98' | 74.7 | 41.7 | 85.2 |
| 'Mercedes' | 81.0 | 15.0 | 73.9 |
| 'MSA-31' | 78.1 | 13.0 | 84.7 |
| 'Delmar' | 79.6 | 12.8 | 63.3 |
| LSD | 17.0 | 5.8 | 6.5 |

TABLE 10

Turfgrass quality ratings from the 2002 National St. Augustinegrass Test established at 3 U.S. locations in full sun. (2002 Data: 1 = poor, 9 = excellent)

| Cultivar | Calhoun, LA | Starkville, MS | Lane, OK |
|---|---|---|---|
| 'MSA-31' | 8.0 | 6.4 | 8.0 |
| 'MSA 2-3-98' | 8.0 | 6.9 | 7.5 |
| 'Mercedes' | 7.7 | 6.6 | 5.7 |
| 'Raleigh' | 7.0 | 6.3 | 5.7 |
| 'Floratam' | 6.0 | 5.4 | 7.3 |
| 'Delmar' | 6.3 | 6.2 | 4.5 |
| LSD | 0.8 | 0.3 | 0.5 |

TABLE 11

Turfgrass quality ratings from the 2002 National St. Augustinegrass Test grown at 8 U.S. locations in full sun. (1 = poor, 9 = excellent)

| Cultivar | Pomona, CA 2003-2006 | Jay, FL 2003-2006 | Griffin, GA 2004- 2006 | Calhoun, LA 2003-2006 | Starkville, MS 2003-2006 |
|---|---|---|---|---|---|
| 'MSA 2-3-98' | 6.2 | 5.4 | 6.8 | 6.8 | 7.5 |
| 'Mercedes' | 6.4 | 5.9 | 7.5 | 6.8 | 7.1 |
| 'MSA-31' | 6.6 | 5.4 | 6.8 | 6.8 | 6.4 |
| 'Raleigh' | 5.8 | 5.2 | 6.6 | 6.6 | 6.5 |
| 'Floratam' | 6.1 | 6.1 | 6.3 | 6.3 | 4.5 |
| 'Delmar' | 5.8 | 4.8 | 7.0 | 6.4 | 6.3 |
| LSD | 1.0 | 1.1 | 1.1 | 0.6 | 0.4 |

| Cultivar | Lane, OK 2003-2006 | Florence, SC 2003-2006 | College Station, TX 2003-2004 | Mean |
|---|---|---|---|---|
| 'MSA 2-3-98' | 6.1 | 6.1 | 5.0 | 6.3 |
| 'Mercedes' | 5.3 | 6.0 | 5.3 | 6.3 |
| 'MSA-31' | 5.1 | 5.5 | 4.8 | 6.0 |
| 'Raleigh' | 6.0 | 5.4 | 4.9 | 5.9 |
| 'Floratam' | 6.6 | 5.1 | 5.8 | 5.8 |
| 'Delmar' | 5.8 | 5.2 | 4.6 | 5.8 |
| LSD | 1.3 | 0.9 | 0.8 | 0.4 |

TABLE 12

Turfgrass quality ratings from the 2002 National St. Augustinegrass Test grown under dense shade at Savannah, GA. (1 = poor, 9 = excellent)

| Cultivar | 2003 | 2004 | 2005 | 2006 | Mean |
|---|---|---|---|---|---|
| 'MSA-31' | 7.2 | 7.6 | 7.6 | 6.6 | 7.2 |
| 'Raleigh' | 6.6 | 7.5 | 6.8 | 6.2 | 6.7 |
| 'MSA 2-3-98' | 6.3 | 7.4 | 7.8 | 5.7 | 6.6 |
| 'Mercedes' | 6.0 | 6.9 | 6.8 | 5.8 | 6.4 |
| 'Delmar' | 5.5 | 7.1 | 6.8 | 6.0 | 6.3 |
| 'Floratam' | 4.7 | 5.5 | 5.3 | 4.5 | 5.0 |
| LSD | 0.9 | 0.7 | 1.1 | 1.6 | 0.6 |

TABLE 13

Density ratings from the 2002 National St. Augustinegrass Test grown under dense shade at Savannah, GA. (1 = low, 9 = high)

| Cultivar | Spring density 2004-06 | Summer density 2004-06 | Fall density 2004-05 |
|---|---|---|---|
| 'MSA-31' | 6.2 | 7.0 | 7.2 |
| 'MSA 2-3-98' | 6.7 | 6.8 | 7.3 |
| 'Raleigh' | 6.8 | 6.2 | 5.8 |
| 'Mercedes' | 5.9 | 5.8 | 5.8 |
| 'Delmar' | 5.6 | 6.2 | 6.3 |
| 'Floratam' | 3.3 | 4.2 | 4.5 |
| LSD | 1.7 | 1.1 | 1.5 |

TABLE 14

Leaf texture ratings from the 2002 National St. Augustinegrass Test. (1 = coarse, 9 = fine)

| Cultivar | Pomona, CA 2003-2005 | Starkville, MS 2003-2006 | Lane, OK 2004-2006 |
|---|---|---|---|
| 'MSA-31' | 5.4 | 7.8 | 5.7 |
| 'MSA 2-3-98' | 5.0 | 6.8 | 5.4 |
| 'Mercedes' | 5.0 | 6.8 | 5.7 |
| 'Raleigh' | 4.9 | 5.8 | 5.4 |
| 'Delmar' | 4.8 | 5.9 | 4.4 |
| 'Floratam' | 3.9 | 4.4 | 4.7 |
| LSD | 1.6 | 0.4 | 0.7 |

| Cultivar | Florence, SC 2003-2005 | College Station, TX 2003 | Mean |
|---|---|---|---|
| 'MSA-31' | 2.0 | 6.0 | 5.6 |
| 'MSA 2-3-98' | 2.0 | 5.7 | 5.1 |
| 'Mercedes' | 1.7 | 6.0 | 5.1 |
| 'Raleigh' | 1.3 | 5.0 | 4.7 |

TABLE 14-continued

Leaf texture ratings from the 2002 National St. Augustinegrass Test. (1 = coarse, 9 = fine)

| | | | |
|---|---|---|---|
| 'Delmar' | 1.0 | 5.7 | 4.4 |
| 'Floratam' | 1.7 | 4.0 | 4.0 |
| LSD | 0.0 | 0.5 | 0.5 |

TABLE 15

Genetic color ratings from the 2002 National St. Augustinegrass Test. (1 = light green, 9 = dark green)

| Cultivar | Pomona, CA 2003-2006 | Jay, FL 2003-2006 | Griffin, GA 2004-2006 | Starkville, MS 2003-2006 |
|---|---|---|---|---|
| 'MSA 2-3-98' | 5.8 | 5.9 | 7.4 | 7.6 |
| 'Mercedes' | 6.5 | 6.2 | 7.9 | 7.1 |
| 'Delmar' | 6.3 | 5.0 | 7.7 | 7.2 |
| 'MSA-31' | 6.5 | 5.8 | 7.8 | 7.4 |
| 'Raleigh' | 5.9 | 5.2 | 7.6 | 6.8 |
| 'Floratam' | 6.5 | 6.1 | 6.7 | 7.0 |
| LSD | 1.6 | 1.0 | 1.1 | 0.7 |

| Cultivar | Lane, OK 2003-2005 | Florence, SC 3003-2005 | College Station, TX 2003 | Mean |
|---|---|---|---|---|
| 'MSA 2-3-98' | 7.2 | 6.3 | 4.7 | 6.5 |
| 'Mercedes' | 5.9 | 6.0 | 4.7 | 6.5 |
| 'Delmar' | 7.4 | 6.2 | 5.0 | 6.5 |
| 'MSA-31' | 6.6 | 5.3 | 4.7 | 6.4 |
| 'Raleigh' | 6.3 | 5.8 | 4.7 | 6.1 |
| 'Floratam' | 5.1 | 5.1 | 6.0 | 6.1 |
| LSD | 0.8 | 0.9 | 0.8 | 0.4 |

TABLE 16

Fall Color (November) ratings from the 2002 National St. Augustinegrass Test. (1 = brown, 9 = completely green)

| Cultivar | Pomona, CA 2003-2005 | Jay, FL 2003-2005 | Griffin, GA 2004 | Lane, OK 2003-2004 | Florence, SC 2004 | Mean |
|---|---|---|---|---|---|---|
| 'MSA-31' | 5.7 | 4.3 | 5.3 | 7.2 | 6.0 | 5.5 |
| 'Floratam' | 4.9 | 5.0 | 4.3 | 7.7 | 5.0 | 5.4 |
| 'Delmar' | 5.2 | 4.0 | 6.3 | 6.7 | 5.0 | 5.2 |
| 'Mercedes' | 5.1 | 4.4 | 6.0 | 5.3 | 5.3 | 5.0 |
| 'MSA 2-3-98' | 4.7 | 4.2 | 5.3 | 5.8 | 4.7 | 4.8 |
| 'Raleigh' | 4.2 | 4.2 | 5.3 | 4.7 | 4.7 | 4.5 |
| LSD | 1.2 | 1.0 | 1.1 | 1.7 | 2.3 | 0.7 |

TABLE 17

Winter color ratings from the 2002 National St. Augustinegrass Test. (1 = brown, 9 = completely green)

| Cultivar | Pomona, CA 2005 | Jay, FL 2005 | College Station, TX 2003 | Mean |
|---|---|---|---|---|
| 'MSA-31' | 5.3 | 2.3 | 4.7 | 4.3 |
| 'Floratam' | 5.3 | 3.0 | 3.3 | 3.8 |
| 'Mercedes' | 5.3 | 3.0 | 3.0 | 3.6 |
| 'MSA 2-3-98' | 4.7 | 2.0 | 3.3 | 3.3 |
| 'Raleigh' | 4.7 | 3.0 | 2.7 | 3.3 |

TABLE 17-continued

Winter color ratings from the 2002 National St. Augustinegrass Test. (1 = brown, 9 = completely green)

| Cultivar | Pomona, CA 2005 | Jay, FL 2005 | College Station, TX 2003 | Mean |
|---|---|---|---|---|
| 'Delmar' | 4.7 | 2.3 | 2.3 | 2.9 |
| LSD | 1.7 | 1.3 | 1.4 | 1.2 |

TABLE 18

Frost tolerance ratings from the 2002 National St. Augustinegrass Test. (1 = brown, 9 = completely green)

| Cultivar | Griffin, GA 2004 | Starkville, MS 2005-2006 | Lane, OK 2003-2006 | Mean |
|---|---|---|---|---|
| 'MSA 2-3-98' | 3.3 | 7.2 | 6.3 | 6.2 |
| 'Mercedes' | 2.3 | 7.0 | 6.4 | 6.0 |
| 'Raleigh' | 4.0 | 6.5 | 5.7 | 5.6 |
| 'MSA-31' | 2.3 | 5.0 | 5.9 | 5.3 |
| 'Delmar' | 2.3 | 5.0 | 5.9 | 5.1 |
| 'Floratam' | 6.7 | 3.2 | 4.3 | 4.3 |
| LSD | 2.4 | 1.1 | 1.3 | 1.0 |

TABLE 19

Percent winterkill estimates from the 2002 National St. Augustinegrass Test.

| Cultivar | Lane, OK 2003-2006 | Florence, SC 2003 | Mean |
|---|---|---|---|
| 'MSA-31' | 57.1 | 43.3 | 60.4 |
| 'Floratam' | 55.0 | 70.0 | 58.3 |
| 'Mercedes' | 40.8 | 6.7 | 39.2 |
| 'MSA 2-3-98' | 39.2 | 2.3 | 38.6 |
| 'Delmar' | 36.3 | 16.7 | 36.4 |
| 'Raleigh' | 33.8 | 11.7 | 34.2 |
| LSD | 17.4 | 14.9 | 17.7 |

TABLE 20

Spring green-up ratings from the 2002 National St. Augustinegrass Test during 2003-2006. (1 = brown, 9 = completely green)

| Cultivar | Pomona, CA 2004-2005 | Jay, FL 2003-2005 | Griffin, GA 2005 | Calhoun, LA 2003-2004 |
|---|---|---|---|---|
| 'Mercedes' | 7.2 | 4.6 | 4.3 | 6.2 |
| 'MSA 2-3-98' | 7.0 | 4.1 | 5.0 | 6.0 |
| 'Delmar' | 5.7 | 4.8 | 4.7 | 6.2 |
| 'Raleigh' | 6.3 | 4.8 | 4.3 | 6.0 |
| 'MSA-31' | 7.8 | 5.4 | 2.0 | 5.2 |
| 'Floratam' | 6.2 | 5.1 | 2.0 | 6.0 |
| LSD | 1.7 | 1.1 | 1.5 | 1.2 |

| Cultivar | Starkville, MS 2003-2006 | Lane, OK 2003-2006 | Florence, SC 2003-2005 | College Station, TX 2004 | Mean |
|---|---|---|---|---|---|
| 'Mercedes' | 5.6 | 4.1 | 3.7 | 2.7 | 4.8 |
| 'MSA 2-3-98' | 6.2 | 3.1 | 3.8 | 2.7 | 4.7 |
| 'Delmar' | 4.3 | 4.5 | 3.7 | 3.3 | 4.5 |

TABLE 20-continued

Spring green-up ratings from the 2002 National St. Augustinegrass Test during 2003-2006. (1 = brown, 9 = completely green)

| | | | | | |
|---|---|---|---|---|---|
| 'Raleigh' | 5.0 | 3.3 | 3.0 | 2.0 | 4.5 |
| 'MSA-31' | 3.1 | 2.2 | 2.9 | 4.0 | 3.7 |
| 'Floratam' | 1.9 | 2.6 | 2.2 | 4.0 | 3.5 |
| LSD | 1.0 | 1.1 | 0.9 | 0.7 | 0.6 |

TABLE 21

Percent living ground cover in spring from the 2002 National St. Augustinegrass Test.

| Cultivar | Pomona, CA 2004-2005 | Calhoun, LA 2003 | Starkville, MS 2003-2006 | Lane, OK 2003-2006 |
|---|---|---|---|---|
| 'Raleigh' | 96.8% | 76.7% | 85.8% | 63.2% |
| 'Mercedes' | 94.3 | 80.0 | 89.4 | 58.3 |
| 'MSA 2-3-98' | 90.2 | 78.3 | 93.1 | 60.4 |
| 'Delmar' | 87.3 | 70.0 | 76.7 | 58.8 |
| 'MSA-31' | 92.8 | 75.0 | 57.9 | 41.0 |
| 'Floratam' | 94.5 | 75.0 | 37.9 | 42.3 |
| LSD | 10.3 | 7.1 | 11.8 | 17.4 |

| Cultivar | Florence, SC 2003 | College Station, TX 2003-2004 | Mean |
|---|---|---|---|
| 'Raleigh' | 5.0% | 84.7% | 74.1% |
| 'Mercedes' | 11.0 | 83.0 | 73.4 |
| 'MSA 2-3-98' | 16.0 | 78.7 | 72.9 |
| 'Delmar' | 15.7 | 67.3 | 66.5 |
| 'MSA-31' | 4.7 | 71.3 | 56.4 |
| 'Floratam' | 1.7 | 92.0 | 55.5 |
| LSD | 7.9 | 19.6 | 9.7 |

TABLE 22

Warm temperature brown patch disease (*Rhizoctonia solani*) rating[a] from the 2002 National St. Augustinegrass Test.

| Cultivar | Florence, SC 2004 | College Station, TX 2003-2004 | Mean |
|---|---|---|---|
| 'Floratam' | 8.3 | 7.8 | 8.3 |
| 'MSA-31' | 8.3 | 7.8 | 8.2 |
| 'MSA 2-3-98' | 6.7 | 7.2 | 7.3 |
| 'Mercedes' | 6.3 | 7.0 | 6.7 |
| 'Raleigh' | 4.3 | 5.8 | 5.6 |
| 'Delmar' | 5.0 | 5.3 | 4.8 |
| LSD | 3.3 | 4.2 | 3.0 |

[a]Disease rating, 1 = severe, 9 = no disease

TABLE 23

Cool temperature brown patch disease (*Rhizoctonia cerealis*) rating[a] from the 2002 National St. Augustinegrass Test.

| Cultivar | Florence, SC 2004-2005 |
|---|---|
| 'MSA-31' | 7.5 |
| 'Floratam' | 6.8 |
| 'Delmar' | 6.3 |
| 'MSA 2-3-98' | 5.8 |
| 'Mercedes' | 5.2 |

TABLE 23-continued

Cool temperature brown patch disease (*Rhizoctonia cerealis*) rating[a] from the 2002 National St. Augustinegrass Test.

| Cultivar | Florence, SC 2004-2005 |
|---|---|
| 'Raleigh' | 3.7 |
| LSD | 2.4 |

[a]Disease rating, 1 = severe, 9 = no disease

TABLE 24

Gray leaf spot ratings from the 2002 National St. Augustinegrass Test.

| | Jay, FL 2003 | Starkville, MS 2005 | Lane, OK 2003 | Mean |
|---|---|---|---|---|
| 'MSA-31' | 8.0 | 6.7 | 8.0 | 7.3 |
| 'MSA 2-3-98' | 8.0 | 4.3 | 5.7 | 7.1 |
| 'Delmar' | 6.7 | 6.7 | 6.0 | 6.5 |
| 'Raleigh' | 4.0 | 7.7 | 6.3 | 6.4 |
| 'Mercedes' | 4.0 | 7.0 | 6.3 | 6.1 |
| 'Floratam' | 6.7 | 4.0 | 8.3 | 5.8 |
| LSD | 2.1 | 1.0 | 1.0 | 1.1 |

Gray leaf spot rating scale: 1 = severe, 9 = no disease

TABLE 25

Take-all patch rating at Lane, OK in 2004.

| Cultivar | Lane, OK 2004 |
|---|---|
| 'Floratam' | 7.3 |
| 'MSA 2-3-98' | 7.0 |
| 'Delmar' | 6.0 |
| 'Raleigh' | 5.7 |
| 'MSA-31' | 4.3 |
| 'Mercedes' | 4.0 |
| LSD | 0.9 |

[a]Disease rating, 1 = severe, 9 = no disease

TABLE 26

Seedhead rating of St. Augustinegrass cultivars at Lane, OK.

| Cultivar | 2003 | 2004 | 2005 | 2006 | Mean |
|---|---|---|---|---|---|
| 'MSA-31' | 6.0 | 7.3 | 9.0 | 6.3 | 7.2 |
| 'Mercedes' | 6.7 | 7.0 | 6.0 | 6.0 | 6.4 |
| 'MSA 2-3-98' | 4.3 | 5.3 | 6.7 | 8.7 | 6.3 |
| 'Floratam' | 8.7 | 5.7 | 4.7 | 4.3 | 5.8 |
| 'Raleigh' | 4.7 | 4.0 | 4.0 | 5.7 | 4.6 |
| 'Delmar' | 4.3 | 2.7 | 3.3 | 6.7 | 4.3 |
| LSD | 1.1 | 1.2 | 1.5 | 2.9 | 1.7 |

Seedhead rating: 9 = no seedheads

TABLE 27

Seedhead rating of St. Augustinegrass cultivars at Starkville, MS.

| Cultivar | Starkville, MS 2003 |
|---|---|
| 'Mercedes' | 8.0 |
| 'MSA-31' | 7.7 |
| 'Floratam' | 7.7 |
| 'MSA 2-3-98' | 7.3 |

TABLE 27-continued

Seedhead rating of St. Augustinegrass cultivars at Starkville, MS.

| Cultivar | Starkville, MS 2003 |
|---|---|
| 'Delmar' | 6.0 |
| 'Raleigh' | 3.3 |
| LSD | 1.0 |

Seedhead rating: 9 = no seedheads

TABLE 28

Horizontal spread rating of St. Augustinegrass cultivars.

| Cultivar | Lane, OK 2004 |
|---|---|
| 'Floratam' | 6.3 |
| 'Mercedes' | 4.7 |
| 'MSA 2-3-98' | 4.3 |
| 'Raleigh' | 4.3 |
| 'Delmar' | 3.3 |
| 'MSA-31' | 3.3 |
| LSD | 2.1 |

Spread rating: 1 = slow, 9 = fast

TABLE 29

Chinch bug counts on St. Augustinegrass cultivars at Griffin, GA in 2006.

| Cultivar | August adult | August nymph | December adult | December nymph | Mean |
|---|---|---|---|---|---|
| 'Raleigh' | 70.7 | 13.3 | 65.7 | 151.7 | 75.3 |
| 'MSA 2-3-98' | 18.0 | 10.0 | 15.7 | 52.3 | 24.0 |
| 'MSA-31' | 25.7 | 6.7 | 6.0 | 24.3 | 15.7 |
| 'Mercedes' | 20.0 | 8.3 | 0.0 | 8.3 | 9.2 |
| 'Delmar' | 12.7 | 0.7 | 0.0 | 5.3 | 4.7 |
| 'Floratam' | 7.0 | 0.3 | 0.0 | 0.3 | 1.9 |
| LSD | 23.5 | 11.8 | 47.3 | 47.9 | 19.8 |

Summary

Observations and analyses on a comparative basis have identified specific characteristics of 'MSA-31' that distinguish it from other St. Augustinegrasses including 'Raleigh', 'Floratam', 'Mercedes', 'Delmar', and various experimental cultivars. 'MSA-31' has excellent turfgrass quality ratings and, particularly, superior quality and density ratings in shade and dense shade that allow it to be produced, marketed, and commercialized as a high quality St. Augustinegrass capable of excellent quality and density ratings in shade in warm climates and in United States Department of Agriculture (USDA) plant hardiness zones 8 and higher. Its superior leaf texture, genetic color, and fall and winter color ratings provide additional distinctions and advantages compared to other St. Augustinegrass cultivars.

As will be apparent to those skilled in horticultural science, the new and distinct perennial St. Augustinegrass variety described herein may vary in minor detail due to climatic, soil, and cultural conditions under which the variety may be grown, as well as the stage of growth.

Comparative DNA Analysis of 'MSA-31' with other Turfgrasses

Randomly Amplified Polymorphic DNA (RAPD) analysis was used to generate DNA fingerprints that uniquely identified 'MSA-31' from other St. Augustinegrasses. All tests and analyses were performed by Juliet D. Tang at Starkville, Miss.

Plants

St. Augustinegrasses were obtained from Wayne Philley at Starkville, Miss. Six turfgrass varieties were tested: 'Sapphire'™, 'Raleigh', 'MSA 2-3-98', 'MSA-31', 'Palmetto'™, and 'Floratam'. Grasses were grown individually in pots in the Institute greenhouse. One block consisted of each plant variety and each block was replicated four (4) times.

DNA Isolation

DNA was extracted from young leaf blades. Plant tissue (100 mg) was pulverized in liquid N2 using a mortar and pestle. Negative controls were subjected to the same procedures, except no plant tissue was added. After extraction, the DNA concentration was determined and all samples were diluted to the same working concentration.

Amplification Primers

Eighty-five ten-mer primers were purchased. Forty-four primers (OPA9, OPAA15, OPAA16, OPAB2, OPAC2, OPAC3, OPAC10, OPAC11, OPAC20, OPAE6, OPAF7, OPAG17, OPAH20, OPAI18, OPAN6, OPAO5, OPAP15, OPAT13, OPAU1, OPAV1, OPAX9, OPB4, OPB9, OPB10, OPB12, OPB15, OPB17, OPBA9, OPBE8, OPBE17, OPBG2, OPC4, OPC8, OPC11, OPC12, OPE2, OPH4, OPJ10, OPK4, OPM5, OPP15, OPP19, OPW15, OPY20) produced DNA fragments that were polymorphic, i.e. band(s) present in one variety and absent in another when tested against one block of grass DNA. Fifteen of these primers (OPA9, OPAC2, OPAC20, OPAH20, OPAI18, OPAU1, OPAX9, OPB4, OPB9, OPB12, OPBA9, OPC4, OPE2, OPH4, OPM5) were then tested against all four blocks of grass DNA. Primers OPAC20, OPAU1, OPBA9, and OPM5 produced consistent and unique fingerprints for 'MSA-31' across all four replicates. An example fingerprint for each primer is exhibited in FIGS. 6 through 9, respectively.

Amplification

Primer-specific amplification of DNA was performed using Takara Taq DNA polymerase the manufacturer's supplied buffer, and 2.5 mM $MgCl_2$ in a polymerase chain reaction (PCR). The hot start method of preheating the DNA (25 ng) five minutes at 95 deg Celsius (C.) prior to the addition of the enzyme-primer master mix was employed. All amplifications were placed in a MyCycler thermal cycler and run with the following program:

1. 2 min at 95 deg C.
2. 30 s at 94 deg C.
3. 1 min at 35 deg C.
4. 2 min at 72 deg C.
5. return to step 2 and cycle 45 times
6. 20 min hold at 60 deg C.
7. infinite hold at 4 deg C.

Gel Electrophoresis and Photography

DNA fragments produced by PCR were separated on a 1.5% agarose gel in Tris-acetate-EDTA buffer, then stained with $EtBr_2$, and visualized using a Versadoc 3000. The lanes of the gel photographs, shown in FIGS. 6 through 9, correspond to (from left to right): Lane 1='Sapphire'™, Lane 2='Raleigh', Lane 3='MSA 2-3-98', Lane 4='MSA-31', Lane 5='Palmetto'™, Lane 6='Floratam', Lane 7=negative control, and Lane 8=100 bp PCR molecular ruler size marker.

RAPD Analysis

For RAPD analysis, bands in the gel images were detected, matched, and sized using QuantityOne software. All samples could be distinguished from the others using one or more of the ten-mer primers. As shown in FIG. 6, 'MSA-31' (Lane 4) shows the presence of the 963 bp band and the absence of the 810 bp band when tested with primer OPAC20. These two bands differentiate 'MSA-31' from the other five cultivars tested. As shown in FIG. 7, 'MSA-31' (Lane 4) shows absences of the 904 bp and the 550 bp bands when tested with primer OPAU1. These two bands differentiate 'MSA-31' from the other five cultivars tested. As shown in FIG. 8, 'MSA-31' shows the absence of the 602 bp band when tested with primer OPBA9. This band differentiates 'MSA-31' from the other five cultivars tested. As shown in FIG. 9, 'MSA-31' shows absences of the 1971 bp and the 1533 bp bands when tested with primer OPM5. These bands differentiate 'MSA-31' from the other five cultivars tested.

What is claimed is:

1. A new and distinct variety of perennial St. Augustinegrass plant, substantially as herein illustrated and described.

* * * * *

'Seville' x 'MSA-10'

↓

'MSA-31'

Figure 1

'Floratam' 'Raleigh' 'MSA 2-3-98' 'MSA-31'

'Floratam' 'Raleigh' 'MSA 2-3-98' 'MSA-31'